United States Patent
Okamoto et al.

(10) Patent No.: US 12,378,181 B2
(45) Date of Patent: Aug. 5, 2025

(54) METHOD FOR PRODUCING ALPHA-ACYLOXYCARBOXYLIC ACID ESTER

(71) Applicant: MITSUBISHI GAS CHEMICAL COMPANY, INC., Chiyoda-ku (JP)

(72) Inventors: Atsushi Okamoto, Niigata (JP); Kyoko Hiraoka, Niigata (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 847 days.

(21) Appl. No.: 17/627,626

(22) PCT Filed: Jul. 9, 2020

(86) PCT No.: PCT/JP2020/026874
§ 371 (c)(1),
(2) Date: Jan. 14, 2022

(87) PCT Pub. No.: WO2021/014988
PCT Pub. Date: Jan. 28, 2021

(65) Prior Publication Data
US 2022/0274909 A1    Sep. 1, 2022

(30) Foreign Application Priority Data
Jul. 19, 2019    (JP) ................ 2019-134070

(51) Int. Cl.
C07C 67/08    (2006.01)
C07B 61/00    (2006.01)

(52) U.S. Cl.
CPC .............. *C07C 67/08* (2013.01); *C07B 61/00* (2013.01)

(58) Field of Classification Search
None
See application file for complete search history.

(56) References Cited

U.S. PATENT DOCUMENTS

| | | |
|---|---|---|
| 2,445,911 A | 7/1948 | Fisher et al. |
| 2,518,456 A | 8/1950 | Fein et al. |
| 2003/0186160 A1 | 10/2003 | Ito |

FOREIGN PATENT DOCUMENTS

| | | |
|---|---|---|
| CN | 1131417 A | 9/1996 |
| CN | 105503594 A | 4/2016 |
| DE | 1 134 670 | 8/1962 |
| JP | 2008-174483 A | 7/2008 |
| JP | 2010077338 A * | 4/2010 |
| WO | WO 2006/064685 A1 | 6/2006 |
| WO | WO 2020/004464 A1 | 1/2020 |
| WO | WO 2020/004465 A1 | 1/2020 |
| WO | WO 2020/004466 A1 | 1/2020 |
| WO | WO 2020/004467 A1 | 1/2020 |

OTHER PUBLICATIONS

Machine generated English language translation of Sugi (JP2008174483, published on Jul. 31, 2008), obtained Dec. 2024 (Year: 2024).*
Machine generated English language translation of Nakamura (JP2010077338, published on Apr. 8, 2010), obtained Dec. 2024 (Year: 2024).*
International Search Report issued Aug. 11, 2020 in PCT/JP2020/026874 filed Jul. 9, 2020, 3 pages.
Giuseppe Bartoli et al., "Zn(ClO$_4$)$_2$:6H$_2$ O as a Powerful Catalyst for a Practical Acylation of Alcohols with Acid Anhydrides", European Journal of Organic Chemistry, 2003, vol. 23 pp. , 4611-4617.
Akihiro Orita et al., "Highly Powerful and Practical Acylation of Alcohols with Acid Anhydride Catalyzed by Bi(OTf)$_3$", Journal of Organic Chemistry, 2001, vol. 66, No. 26, pp. 8926-8934.
M. L. Fein et al. "Acetylation of Alkyl Lactates and Similar Hydroxy Esters with Acetic Acid", Industrial and Engineering Chemistry, 1948, vol. 40, No. 3, pp. 534-538.
N. K. Kobyakova et al., "Intermediate Step of the Catalytic Conversion of Acetone Cyanohydrin Into Methacrylic Acid", Russian Journal of Applied Chemistry, 1993, vol. 66, No. 6, pp. 1058-1062.
Fabian Weber, et al., "Total Syntheses of the Dihydrofuranonecarboxylate Natural Products Gregatin B and E: Gram-Scale Synthesis of (+)-Gregatin B and Unambiguous Assignment of the Stereostructure of (+)-Gregatin E," Organic Letters, vol. 16, XP055952210, 2014, pp. 6428-6431.

* cited by examiner

*Primary Examiner* — Amy C Bonaparte
(74) *Attorney, Agent, or Firm* — Oblon, McClelland, Maier & Neustadt, L.L.P.

(57) ABSTRACT

A method for producing an α-acyloxycarboxylic acid ester of Formula (1) is described. The method involves reacting an α-hydroxycarboxylic acid ester compound with an acylating agent in the presence of a catalyst comprising an iron halide compound. $R^1$ represents a hydrogen atom, a methyl group, an ethyl group, an n-propyl group, an isopropyl group, or a tert-butyl group, $R^2$ and $R^3$ each independently represent a methyl group or an ethyl group, and $R^4$ represents a linear, branched, or cyclic alkyl group having from 1 to 6 carbon atoms.

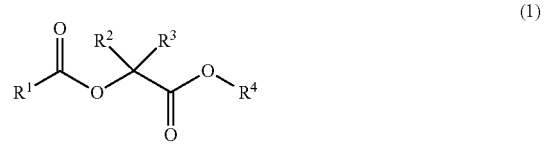

(1)

20 Claims, No Drawings

METHOD FOR PRODUCING ALPHA-ACYLOXYCARBOXYLIC ACID ESTER

CROSS-REFERENCE TO RELATED APPLICATIONS

The present application is a 35 U.S.C. § 371 national stage application of International patent application PCT/JP2020/026874, filed Jul. 9, 2020, which is based on and claims the benefit of priority to Japanese Application No. 2019-134070, filed Jul. 19, 2019. The entire contents of these applications are incorporated herein by reference.

TECHNICAL FIELD

The present invention relates to a method for producing an α-acyloxycarboxylic acid ester by reacting an α-hydroxycarboxylic acid ester with an acylating agent.

BACKGROUND ART

Reaction of esterifying an alcohol with an acylating agent is a very common method in organic chemistry. A method of acylating (esterifying) the alcohol moiety of an α-hydroxycarboxylic acid ester with an acylating agent is also well known. However, most of the reaction examples in which an α-hydroxycarboxylic acid ester is acylated with an acylating agent are related to lactic acid esters, and document examples thereof include Patent Document 1, Non-Patent Document 1, and Non-Patent Document 2, which include descriptions of a great many types of catalyst examples including citations. The documents specifically describe carboxylates of alkali metals or alkaline earth metals, cobalt chloride, zinc chloride, magnesium bromide, tributylphosphine, trimethylsilyl chloride, scandium triflate, trimethylsilyl triflate, bismuth triflate, magnesium perchlorate, zinc perchlorate, N,N-dimethyl-4-aminopyridine, and the like.

As report examples of an acylating reaction of an α-hydroxycarboxylic acid ester at its alcohol moiety by an acylating agent, the α-hydroxycarboxylic acid ester having a carbon at the α-position not bonded to hydrogen but being substituted with two alkyl groups, for example, Non-Patent Document 3 and Patent Document 2 each describe a method for synthesizing an α-acetoxyisobutyric acid ester from an α-hydroxyisobutyric acid ester using acetic acid as an acylating agent and sulfuric acid as a catalyst.

Non-Patent Document 4 describes a method for synthesizing methyl α-acetoxyisobutyrate from methyl α-hydroxyisobutyrate using acetic anhydride as an acylating agent and hydrochloric acid as a catalyst.

Patent Document 3 describes a method for synthesizing methyl α-acetoxyisobutyrate from methyl α-hydroxyisobutyrate using acetic anhydride as an acylating agent and concentrated sulfuric acid as a catalyst.

CITATION LIST

Patent Documents

Patent Document 1: German Patent No. 1,134,670
Patent Document 2: U.S. Pat. No. 2,518,456
Patent Document 3: U.S. Pat. No. 2,445,911

Non-Patent Documents

Non-Patent Document 1: European Journal of Organic Chemistry, 2003, 23, 4611-4617.
Non-Patent Document 2: Journal of Organic Chemistry, 2001, 66 (26), 8926-8934.
Non-Patent Document 3: INDUSTRIAL AND ENGINEERING CHEMISTRY, 1948, Vol. 40, No. 3, Page 534-538.
Non-Patent Document 4: Journal of Applied Chemistry of USSR, 1993, Vol. 66, No. 6, Page 1058-1062.

DISCLOSURE OF THE INVENTION

Technical Problem

In the methods described in Non-Patent Document 3 and Patent Document 2, a considerable amount of α-acetoxyisobutyric acid is formed as a byproduct, and thus, the yield of the intended α-acetoxyisobutyric acid ester is not sufficient. Non-Patent Document 4 and Patent Document 3 do not describe the yield of the synthesis reaction, and Non-Patent Document 4 only describes an isolation yield of 47.5 mol %.

In an acylating reaction of an α-hydroxycarboxylic acid ester at its alcohol moiety by an acylating agent, the α-hydroxycarboxylic acid ester having a carbon at the α-position not bonded to hydrogen but being substituted with two alkyl groups, there are concerns in comparison with a lactic acid ester as follows: 1) the hydroxyl group at the α-position is likely to be eliminated by an acid catalyst, and an unsaturated carboxylic acid ester is likely to be formed; 2) the carbon at the α-position has many substituents, and due to the steric hindrance thereof, the acylation reaction of the hydroxyl group at the α-position does not readily proceed or more severe reaction conditions are required; and the like. Accordingly, the reaction is expected to be more disadvantageous from the perspective of reaction selectivity and yield.

An object of the present invention is to provide a method for producing an α-acyloxycarboxylic acid ester, the method being efficient and excellent in economic efficiency.

Solution to Problem

The present inventors have extensively conducted studies on a method for producing an α,α-dialkyl-α-acyloxycarboxylic acid ester (hereinafter, also simply referred to as "α-acyloxycarboxylic acid ester") by reacting an α, α-dialkyl-α-hydroxycarboxylic acid ester (herein, also simply referred to as "α-hydroxycarboxylic acid ester"), which has the carbon at the α-position not bonded to hydrogen but being substituted with two alkyl groups, with an acylating agent, and discovered that when the reaction is performed in the presence of a small amount of an inexpensive catalyst including an iron halide compound, an α-acyloxycarboxylic acid ester can be produced in a high yield under mild reaction conditions.

That is, the present invention is as follows.

<1> A method for producing an α-acyloxycarboxylic acid ester compound represented by Formula (1) below, including reacting an α-hydroxycarboxylic acid ester compound represented by Formula (2) below with an acylating agent represented by Formula (3) below in the presence of a catalyst comprising an iron halide compound:

[Chem. 1]

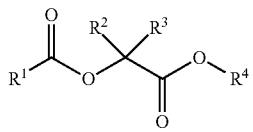
(1)

where $R^1$ represents a hydrogen atom, a methyl group, an ethyl group, a n-propyl group, an isopropyl group, or a tert-butyl group, $R^2$ and $R^3$ each independently represent a methyl group or an ethyl group, and $R^4$ represents a linear, branched, or cyclic alkyl group having from 1 to 6 carbon atoms;

[Chem. 2]

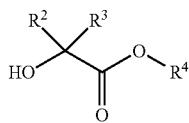
(2)

where $R^2$, $R^3$, and $R^4$ are the same respectively as $R^2$, $R^3$, and $R^4$ in Formula (1); and

[Chem. 3]

(3)

where $R^1$ is the same as $R^1$ in Formula (1), Z is chlorine, bromine, or an acyloxy group represented by $R^5C(=O)O—$, and $R^5$ represents a hydrogen atom, a methyl group, an ethyl group, a n-propyl group, an isopropyl group, or a tert-butyl group.

<2> The production method according to <1>, wherein the catalyst including an iron halide compound is one selected from $FeCl_3$, $FeBr_3$, $FeCl_2$, $FeBr_2$, hydrates thereof, and complexes with a ligand coordinated thereto, or a mixture of two or more thereof.

<3> The production method of making <1> or <2>, wherein the catalyst including an iron halide compound is one selected from $FeCl_3$, a hydrate thereof, and a complex with a ligand coordinated thereto, or a mixture of two or more thereof.

<4> The production method according to any one of <1> to <3>, wherein the acylating agent is a carboxylic anhydride represented by Formula (7) below:

[Chem. 4]

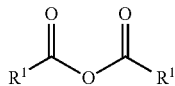
(7)

where $R^1$ is the same as $R^1$ in Formula (1).

<5> The production method according to any one of <1> to <4>, wherein, in the ester compound represented by Formula (1), $R^4$ is selected from the group consisting of a methyl group, an ethyl group, a n-propyl group, an isopropyl group, a n-butyl group, an isobutyl group, a sec-butyl group, a tert-butyl group, a 2-methylbutyl group, a 3-methylbutyl group, a 2-methylpentyl group, a 2,2-dimethylpropyl group, a 4-methylpentan-2-yl group, a cyclopentyl group, a cyclohexyl group, and a n-hexyl group.

<6> The production method according to any one of <1> to <5>, wherein $R^2$ and $R^3$ are both methyl groups in the ester compound represented by Formula (1).

<7> The method of any one of <1> to <6>, wherein the reaction is performed in absence of a solvent.

Advantageous Effects of Invention

According to the present invention, it is possible to provide a method for producing an α-acyloxycarboxylic acid ester, the method being efficient and excellent in economic efficiency.

DESCRIPTION OF EMBODIMENTS

[Method for Producing α-Acyloxycarboxylic Acid Ester]

In the method for producing an α-acyloxycarboxylic acid ester of the present embodiment (hereinafter, also simply referred to as "the present production method"), an α-hydroxycarboxylic acid ester represented by Formula (2) below is reacted with an acylating agent represented by Formula (3) below in the presence of a catalyst including an iron halide compound (hereinafter, also simply referred to as "the present catalyst") to form an α-acyloxycarboxylic acid ester represented by Formula (1) below:

[Chem. 5]

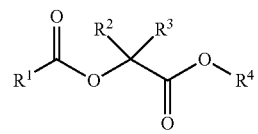
(1)

where $R^1$ represents a hydrogen atom, a methyl group, an ethyl group, a n-propyl group, an isopropyl group, or a tert-butyl group, $R^2$ and $R^3$ each independently represent a methyl group or an ethyl group, and $R^4$ represents a linear, branched, or cyclic alkyl group having from 1 to 6 carbon atoms;

[Chem. 6]

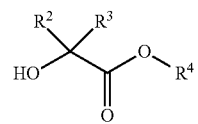
(2)

where $R^2$, $R^3$, and $R^4$ are the same respectively as $R^2$, $R^3$, and $R^4$ in Formula (1); and

[Chem. 7]

(3)

where $R^1$ is the same as $R^1$ in Formula (1), Z is chlorine, bromine, or an acyloxy group represented by $R^5C(=O)O—$, and $R^5$ represents a hydrogen atom, a methyl group, an ethyl group, a n-propyl group, an isopropyl group, or a tert-butyl group.

The reaction for formation of the α-acyloxycarboxylic acid ester of the present production method is represented by Formula (4) below:

[Chem. 8]

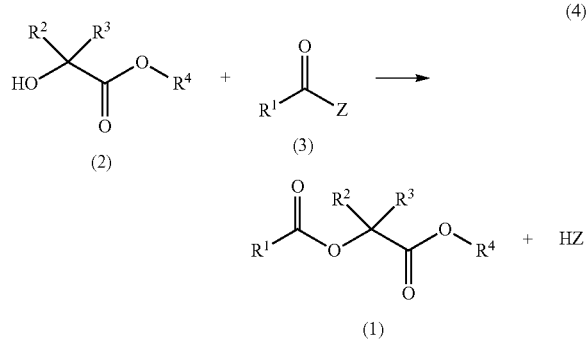
(4)

where $R^1$, $R^2$, $R^3$, $R^4$, and Z are the same as $R^1$, $R^2$, $R^3$, $R^4$, and Z in Formulas (1) to (3) above respectively.

<α-Hydroxycarboxylic Acid Ester>

One of the raw material compounds used in the production method is an α-hydroxycarboxylic acid ester represented by Formula (2) above. Specific examples include α-hydroxyisobutyric acid ester ($R^2$=methyl group, $R^3$=methyl group), α-hydroxy-2-methylbutanoic acid ester ($R^2$=methyl group, $R^3$=ethyl group), and α-hydroxy-2-ethylbutanoic acid ester ($R^2$=ethyl group, $R^3$=ethyl group).

Among these, from the perspective of ease of availability and an excellent reaction yield, both $R^2$ and $R^3$ are preferably methyl groups. That is, the compound represented by Formula (2) is preferably an α-hydroxyisobutyric acid ester.

Each of these esters has an $R^4$ group in the molecule, which represents a linear, branched or cyclic alkyl group having 1 to 6 carbon atoms. Specific examples thereof include a methyl group, an ethyl group, a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group (2-pentyl group), a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a n-hexyl group, a 1-methylpentyl group (2-hexyl group), a 2-methylpentyl group, a 3-methylpentyl group, a 4-methylpentyl group, a 2-methylpentan-2-yl group, a 2,2-dimethylbutyl group, a 3,3-dimethylbutyl group, a 3-methylpentan-2-yl group, a 2,3-dimethylbutyl group, a 4-methylpentan-2-yl group, a 3-hexyl group, a 2-ethylbutyl group, a 2,3-dimethylbutan-2-yl group, a 3,3-dimethylbutan-2-yl group, a 4-methylpentan-3-yl group, a cyclopropyl group, a cyclobutyl group, a cyclopentyl group, and a cyclohexyl group.

Among these, from the perspective of ease of availability, $R^4$ is preferably a methyl group, an ethyl group, a n-propyl group, an isopropyl group, a n-butyl group, an isobutyl group, a sec-butyl group, a tert-butyl group, a 2-methylbutyl group, a 3-methylbutyl group, a neopentyl group (2,2-dimethylpropyl group), a n-hexyl group, a 2-methylpentyl group, a 4-methylpentan-2-yl group, a cyclopentyl group or a cyclohexyl group, more preferably a methyl group, an ethyl group, an n-propyl group, an isopropyl group, a n-butyl group, an isobutyl group, a sec-butyl group, a tert-butyl group, or a n-hexyl group, further preferably a methyl group, an ethyl group, a n-propyl group, an isopropyl group, a n-butyl group, an isobutyl group, or a sec-butyl group, further more preferably a methyl group or an isopropyl group.

These α-hydroxycarboxylic acid esters may have one or more asymmetric carbons derived from the combination of the $R^2$ group and the $R^3$ group and the structure of the $R^4$ group. Any one of resulting stereoisomers or a mixture of two or more of the stereoisomers at any ratio is also included in the raw material compound of the present production method.

One type of α-hydroxycarboxylic acid esters represented by Formula (2) may be used alone or two or more types of these may be used in combination.

α-Hydroxycarboxylic acid esters that are industrially easily available and easily utilized are α-hydroxyisobutyric acid esters. Specific examples thereof include methyl α-hydroxyisobutyrate, ethyl α-hydroxyisobutyrate, n-propyl α-hydroxyisobutyrate, isopropyl α-hydroxyisobutyrate, n-butyl α-hydroxyisobutyrate, isobutyl (2-methylpropyl) α-hydroxyisobutyrate, sec-butyl (butane-2-yl) α-hydroxyisobutyrate, tert-butyl (1,1-dimethylethyl) α-hydroxyisobutyrate, 2-methylbutyl α-hydroxyisobutyrate, 3-methylbutyl α-hydroxyisobutyrate, 2,2-dimethylpropyl α-hydroxyisobutyrate, n-hexyl α-hydroxyisobutyrate, 2-methylpentyl α-hydroxyisobutyrate, 4-methylpentan-2-yl α-hydroxyisobutyrate, cyclopentyl α-hydroxyisobutyrate, and cyclohexyl α-hydroxyisobutyrate.

The raw material for synthesis or production process of the α-hydroxycarboxylic acid ester represented by Formula (2) used in the present production method is not particularly limited, and those produced by a known method can be used.

<Acylating Agent>

One of the raw material compounds used in the present production method is an acylating agent represented by Formula (3) above. Examples thereof include a carboxylic acid chloride, a carboxylic acid bromide, and a carboxylic anhydride.

Specific examples of the carboxylic acid chloride include acetyl chloride, propanoyl chloride, n-butyryl chloride, isobutyryl chloride, and pivaloyl chloride.

Specific examples of the carboxylic acid bromide include acetyl bromide, propanoyl bromide, n-butyryl bromide, isobutyryl bromide, and pivaloyl bromide.

Specific examples of the carboxylic anhydride include acetic anhydride, propionic anhydride, butyric anhydride, isobutyric anhydride, pivalic anhydride, formic acetic anhydride, acetic propionic anhydride, acetic butyric anhydride, acetic isobutyric anhydride, and acetic pivalic anhydride.

One type of acylating agents may be used alone, or two or more types of these may be used in combination.

The raw material for synthesis or production process of the acylating agent used in the production method is not particularly limited, and those produced by a known method can be used.

When a carboxylic acid chloride is used as the acylating agent, hydrogen chloride (hydrochloric acid) is formed as a by-product, when a carboxylic acid bromide is used, hydrogen bromide is formed as a by-product, and when a carboxylic anhydride is used, a carboxylic acid is formed as a by-product. If production of such by-products is not favorable, such by-products may be neutralized by having a basic neutralizing agent coexist or adding such basic neutralizing agent.

In particular, when hydrogen chloride or hydrogen bromide, which is strongly acidic, is formed as a by-product, it is preferable to neutralize these by using a basic substance such as a hydroxide or a carbonate of an alkali metal or alkaline earth metal, or triethylamine or pyridine as a neutralizing agent. As the amount of the neutralizing agent to be added, it is preferable to use the neutralizing agent in an approximately amount equimolar to hydrogen chloride or hydrogen bromide to be produced.

A carboxylic acid, which is a weakly acidic substance, may not be necessarily neutralized if formed as a by-product, but may be neutralized using a basic substance such as a hydroxide or a carbonate of an alkali metal or alkaline earth metal, or triethylamine or pyridine as a neutralizing agent.

Carboxylic anhydrides are industrially readily available and thus suitably used. Here, when a carboxylic anhydride composed of a different carboxylic acid compound as represented by Formula (5) below is used, the reaction for formation of the α-acyloxycarboxylic acid ester of the present production method forms various product species as represented by Formula (6) below. This complicates the production considering separation and purification of each product:

[Chem. 9]

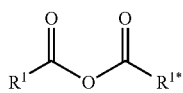

(5)

where $R^1$ is the same as $R^1$ in Formula (1); $R^{1*}$ is the same as $R^1$ in Formula (1); provided that $R^1$ and $R^{1*}$ are different.

[Chem. 10]

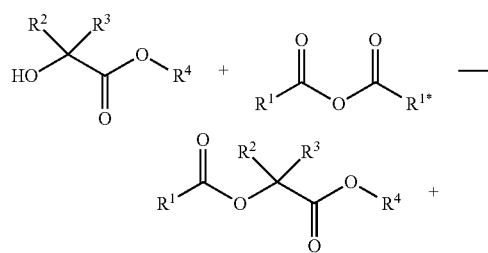

(6)

-continued

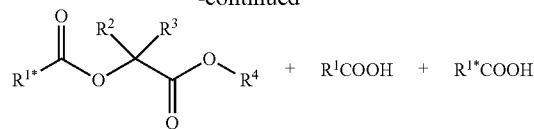

Therefore, use of a carboxylic anhydride composed of a single carboxylic acid compound as represented by Formula (7) below is preferred because a single acylated product is formed and the separation and purification steps of the reaction product can be simplified. The reaction for formation of an α-acyloxycarboxylic acid ester of the present production method using a carboxylic anhydride composed of a single carboxylic acid compound is represented by Formula (8) below:

[Chem. 11]

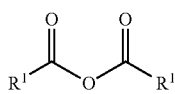

(7)

where $R^1$ is the same as $R^1$ in Formula (1).

[Chem. 12]

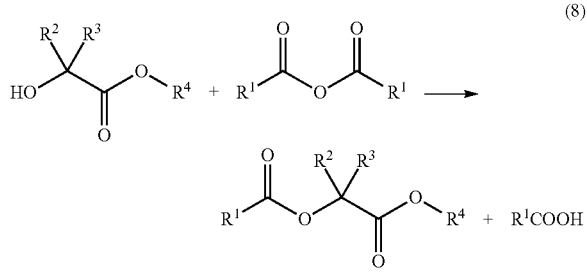

(8)

Specific examples of the carboxylic anhydride composed of a single carboxylic acid compound represented by Formula (7) above include acetic anhydride, propionic anhydride, butyric anhydride, isobutyric anhydride, and pivalic anhydride.

The ratio of the α-hydroxycarboxylic acid ester to the acylating agent used in the production method is not limited. However, the reaction is basically an equimolar reaction. Thus, employing an extreme ratio is not preferred because either one of these may be left in a large amount. For this reason, the molar ratio of the α-hydroxycarboxylic acid ester/acylating agent used in the production method ranges preferably from 0.05 to 20, more preferably from 0.1 to 10, further preferably from 0.5 to 2.0, further more preferably from 0.9 to 1.1.

For complete conversion of the α-hydroxycarboxylic acid ester, the acylating agent is preferably used at least in an equivalent molar amount to α-hydroxycarboxylic acid ester, or greater amount with respect to the α-hydroxycarboxylic acid ester.

In the case where the α-acyloxycarboxylic acid ester is not easily separated from the unreacted acylating agent, the acylating agent is used in an equivalent molar amount or less with respect to the α-hydroxycarboxylic acid ester to completely convert the acylating agent, and thus a problem can be avoided.

As described above, the ratio of the α-hydroxycarboxylic acid ester to the acylating agent can be appropriately selected and used in accordance with the purpose.

<α-Acyloxycarboxylic Acid Ester>

The α-acyloxycarboxylic acid ester formed by the present production method is represented by Formula (1) above.

As represented by Formula (4) above, the acyl group moiety containing the $R^1$ group of the acylating agent is reacted with the hydroxyl group moiety of α-hydroxyisobutyric acid ester ($R^2$ is a methyl group, $R^3$ is a methyl group), α-hydroxy-2-methylbutanoic acid ester ($R^2$ is a methyl group, $R^3$ is an ethyl group), or α-hydroxy-2-ethylbutanoic acid ester ($R^2$ is an ethyl group, $R^3$ is an ethyl group) to form an ester bond, whereby a structure as represented by Formula (1) above is formed.

Specific examples of the α-acyloxycarboxylic acid ester formed when α-hydroxyisobutyric acid ester is used as the α-hydroxycarboxylic acid ester include methyl α-formyloxyisobutyrate, ethyl α-formyloxyisobutyrate, n-propyl α-formyloxyisobutyrate, isopropyl α-formyloxyisobutyrate, n-butyl α-formyloxyisobutyrate, isobutyl α-formyloxyisobutyrate (2-methylpropyl α-formyloxyisobutyrate), sec-butyl α-formyloxyisobutyrate (butan-2-yl α-formyloxyisobutyrate), tert-butyl α-formyloxyisobutyrate (1,1-dimethylethyl α-formyloxyisobutyrate), 2-methylbutyl α-formyloxyisobutyrate, 3-methylbutyl α-formyloxyisobutyrate, 2,2-dimethylpropyl α-formyloxyisobutyrate, 2-methylpentyl α-formyloxyisobutyrate, 4-methylpentan-2-yl α-formyloxyisobutyrate, cyclopentyl α-formyloxyisobutyrate, cyclohexyl α-formyloxyisobutyrate, and n-hexyl α-formyloxyisobutyrate;

methyl α-acetoxyisobutyrate, ethyl α-acetoxyisobutyrate, n-propyl α-acetoxyisobutyrate, isopropyl α-acetoxyisobutyrate, n-butyl α-acetoxyisobutyrate, isobutyl α-acetoxyisobutyrate (2-methylpropyl α-acetoxyisobutyrate), sec-butyl α-acetoxyisobutyrate (butan-2-yl α-acetoxyisobutyrate), tert-butyl α-acetoxyisobutyrate (1,1-dimethylethyl α-acetoxyisobutyrate), 2-methylbutyl α-acetoxyisobutyrate, 3-methylbutyl α-acetoxyisobutyrate, 2,2-dimethylpropyl α-acetoxyisobutyrate, 2-methylpentyl α-acetoxyisobutyrate, 4-methylpentan-2-yl α-acetoxyisobutyrate, cyclopentyl α-acetoxyisobutyrate, cyclohexyl α-acetoxyisobutyrate, and n-hexyl α-acetoxyisobutyrate;

methyl α-propanoyloxyisobutyrate, ethyl α-propanoyloxyisobutyrate, n-propyl α-propanoyloxyisobutyrate, isopropyl α-propanoyloxyisobutyrate, n-butyl α-propanoyloxyisobutyrate, isobutyl α-propanoyloxyisobutyrate (2-methylpropyl α-propanoyloxyisobutyrate), sec-butyl α-propanoyloxyisobutyrate (butan-2-yl α-propanoyloxyisobutyrate), tert-butyl α-propanoyloxyisobutyrate (1,1-dimethylethyl α-propanoyloxyisobutyrate), 2-methylbutyl α-propanoyloxyisobutyrate, 3-methylbutyl α-propanoyloxyisobutyrate, 2,2-dimethylpropyl α-propanoyloxyisobutyrate, 2-methylpentyl α-propanoyloxyisobutyrate, 4-methylpentan-2-yl α-propanoyloxyisobutyrate, cyclopentyl α-propanoyloxyisobutyrate, cyclohexyl α-propanoyloxyisobutyrate, and n-hexyl α-propanoyloxyisobutyrate;

methyl α-n-butyryloxyisobutyrate, ethyl α-n-butyryloxyisobutyrate, n-propyl α-n-butyryloxyisobutyrate, isopropyl α-n-butyryloxyisobutyrate, n-butyl α-n-butyryloxyisobutyrate, isobutyl α-n-butyryloxyisobutyrate (2-methylpropyl α-n-butyryloxyisobutyrate), sec-butyl α-n-butyryloxyisobutyrate (butan-2-yl α-n-butyryloxyisobutyrate), tert-butyl α-n-butyryloxyisobutyrate (1,1-dimethylethyl α-n-butyryloxyisobutyrate), 2-methylbutyl α-n-butyryloxyisobutyrate, 3-methylbutyl α-n-butyryloxyisobutyrate, 2,2-dimethylpropyl α-n-butyryloxyisobutyrate, 2-methylpentyl α-n-butyryloxyisobutyrate, 4-methylpentan-2-yl α-n-butyryloxyisobutyrate, cyclopentyl α-n-butyryloxyisobutyrate, cyclohexyl α-n-butyryloxyisobutyrate, and n-hexyl α-n-butyryloxyisobutyrate;

methyl α-isobutyryloxyisobutyrate, ethyl α-isobutyryloxyisobutyrate, n-propyl α-isobutyryloxyisobutyrate, isopropyl α-isobutyryloxyisobutyrate, n-butyl α-isobutyryloxyisobutyrate, isobutyl α-isobutyryloxyisobutyrate (2-methylpropyl α-isobutyryloxyisobutyrate), sec-butyl α-isobutyryloxyisobutyrate (butan-2-yl α-isobutyryloxyisobutyrate), tert-butyl α-isobutyryloxyisobutyrate (1,1-dimethylethyl α-isobutyryloxyisobutyrate), 2-methylbutyl α-isobutyryloxyisobutyrate, 3-methylbutyl α-isobutyryloxyisobutyrate, 2,2-dimethylpropyl α-isobutyryloxyisobutyrate, 2-methylpentyl α-isobutyryloxyisobutyrate, 4-methylpentan-2-yl α-isobutyryloxyisobutyrate, cyclopentyl α-isobutyryloxyisobutyrate, cyclohexyl α-isobutyryloxyisobutyrate, and n-hexyl α-isobutyryloxyisobutyrate; and methyl α-pivaloyloxyisobutyrate, ethyl α-pivaloyloxyisobutyrate, n-propyl α-pivaloyloxyisobutyrate, isopropyl α-pivaloyloxyisobutyrate, n-butyl α-pivaloyloxyisobutyrate, isobutyl α-pivaloyloxyisobutyrate (2-methylpropyl α-pivaloyloxyisobutyrate), sec-butyl α-pivaloyloxyisobutyrate (butan-2-yl α-pivaloyloxyisobutyrate), tert-butyl α-pivaloyloxyisobutyrate (1,1-dimethylethyl α-pivaloyloxyisobutyrate), 2-methylbutyl α-pivaloyloxyisobutyrate, 3-methylbutyl α-pivaloyloxyisobutyrate, 2,2-dimethylpropyl α-pivaloyloxyisobutyrate, 2-methylpenty α-pivaloyloxyisobutyrate, 4-methylpentan-2-yl α-pivaloyloxyisobutyrate, cyclopentyl α-pivaloyloxyisobutyrate, cyclohexyl α-pivaloyloxyisobutyrate, and n-hexyl α-pivaloyloxyisobutyrate.

Examples of the α-acyloxycarboxylic acid ester formed by the present production method include α-acyloxy-2-methylbutanoic acid ester and α-acyloxy-2-ethylbutanoic acid ester formed by using α-hydroxy-2-methylbutanoic acid ester or α-hydroxy-2-ethylbutanoic acid ester, instead of the raw material for α-acyloxyisobutyric acid ester for which α-hydroxyisobutyric acid ester is used as a raw material, as mentioned above.

<Catalyst>

The catalyst used in the present production method can be a catalyst including an iron halide compound. Note that, in an embodiment of the present invention, the "catalyst including an iron halide compound" is not particularly limited as long as it contains an iron halide compound as the catalyst component, and other catalyst component may be used in combination.

When other catalyst component is used in combination, the content of the iron halide compound is preferably 50 mass % or greater, more preferably 70 mass % or greater, further preferably 90 mass % or greater, and may be 100 mass % with respect to the total catalyst.

Examples of the iron halide include $FeCl_3$, $FeBr_3$, $FeCl_2$, and $FeBr_2$. Examples of the iron halide compound that can be used include anhydrides and hydrates thereof, complexes with a ligand coordinated thereto, and double salts.

Among these, from the perspective of availability and reactivity, the iron halide compound is preferably any one selected from $FeCl_3$, hydrates thereof, and complexes with a ligand coordinated thereto or a mixture of two or more of these.

Specific examples include $FeCl_3$, $FeCl_3 \cdot 2H_2O$, $FeCl_3 \cdot 2.5H_2O$, $FeCl_3 \cdot 3.5H_2O$, $FeCl_3 \cdot 6H_2O$, $FeCl_2$, $FeCl_2 \cdot H_2O$, $FeCl_2 \cdot 2H_2O$, $FeCl_2 \cdot 4H_2O$, $FeCl_2 \cdot 6H_2O$, $FeBr_3$, $FeBr_3 \cdot 6H_2O$, $FeBr_2$, $FeBr_2 \cdot 2H_2O$, $FeBr_2 \cdot 4H_2O$, $FeBr_2 \cdot 6H_2O$, and $FeBr_2 \cdot 9H_2O$. In addition, complexes with a known ligand coordinated to the iron atom in an iron halide compound can be used, where the known ligand includes a nitrogen-containing ligand having a nitrogen atom in the molecule, such as ammonia, alkylamine, pyridine, alkylpyridine, piperidine, and piperazine or a phosphorus-containing ligand having a phosphorous atom in the molecule, such as phosphine, alkylphosphine, phosphine oxide, and alkylphosphine oxide.

In addition, it is possible to use $2FeCl_2 \cdot FeCl_3$ ($Fe_3Cl_7$) and $FeCl_2 \cdot 2FeCl_3$ ($Fe_3Cl_8$), which are double salts formed of $FeCl_2$ and $FeCl_3$; $2FeBr_2 \cdot FeBr_3$ ($Fe_3Br_7$) and $FeBr_2 \cdot 2FeBr_3$ ($Fe_3Br_8$), which are double salts formed of $FeBr_2$ and $FeBr_3$, and hydrates thereof, and complexes with a known ligand coordinated to the iron atom in an iron halide compound.

Further, it is also possible to use $KCl \cdot FeCl_2$ ($KFeCl_3$), $2KCl \cdot FeCl_2$ ($K_2FeCl_4$), $2KCl \cdot FeCl_3$ ($K_2FeCl_5$), $3KCl \cdot NaCl \cdot FeCl_2$ ($K_3NaFeCl_6$), which are double salts formed of $FeCl_2$ or $FeCl_3$ and other element compounds, and hydrates thereof, complexes with a known ligand coordinated to the iron atom in an iron halide compound, and the like.

One selected from these or a mixture of two or more of these at any ratio can be used as the present catalyst.

It is preferable to use a catalyst including a ferric (trivalent iron) halide compound as the present catalyst because the catalyst is produced inexpensively and has excellent stability and reaction activity. Among these, it is more preferable to use $FeCl_3$, $FeCl_3 \cdot 6H_2O$, $FeBr_3$, or $FeBr_3 \cdot 6H_2O$ as an extremely inexpensive ferric halide compound that can be produced industrially easily, and among these, it is particularly preferable to use $FeCl_3$ or $FeCl_3 \cdot 6H_2O$, which has excellent catalytic activity.

There is no restriction on the ratio of the α-hydroxycarboxylic acid ester to the catalyst used in the present production method. The present catalyst has extremely high activity, and thus, the molar ratio, (iron atoms in the iron halide compound)/(α-hydroxycarboxylic acid ester), of iron atoms in the iron halide compound which is a catalyst for the α-hydroxycarboxylic acid ester ranges preferably from $5 \times 10^{-6}$ to $50 \times 10^{-2}$, more preferably from $20 \times 10^{-6}$ to $10 \times 10^{-2}$, further preferably from $50 \times 10^{-6}$ to $1 \times 10^{-2}$.

<Reaction>

The reaction of the present production method is not particularly limited as long as the reaction is performed while the α-hydroxycarboxylic acid ester is in contact with the acylating agent in the presence of the catalyst. The reaction can be performed, for example, in a gas phase or a liquid phase. The catalyst of the present production method is highly active and exhibits a sufficient reaction rate at a low reaction temperature. Under the temperature conditions under which sufficient catalytic activity can be achieved, the reaction raw materials are often both liquids. Thus, the reaction can be performed under a liquid phase and is preferably performed under a liquid phase.

The present production method may be performed by adding a reaction solvent to the α-hydroxycarboxylic acid ester, the acylating agent, and the catalyst. The reaction solvent used in this case is not particularly limited as long as the reaction solvent is inert to the reaction.

Examples of the solvent that can be used include aliphatic saturated hydrocarbons, aliphatic halogenated hydrocarbons, ether compounds, ester compounds, and amide compounds. More specific examples of the solvent include aliphatic saturated hydrocarbons such as n-pentane, isopentane, n-hexane, isohexane, 2,2-dimethyl-butane, n-heptane, isoheptane, 2,2,4-trimethylpentane, n-octane, isooctane, n-nonane, isononane, n-decane, n-pentadecane, cyclohexane, methylcyclohexane, dimethylcyclohexane, and decalin;

aliphatic halogenated hydrocarbons such as chloromethane, chloroethane, dichloromethane, chloroform, carbon tetrachloride, dichloroethane, dichloropropane, bromomethane, bromoethane, and bromoform;

ester compounds such as methyl acetate, ethyl acetate, butyl acetate, methyl propionate, methyl n-butyrate, ethyl n-butyrate, butyl n-butyrate, methyl isobutyrate, cyclohexyl n-butyrate, cyclohexyl isobutyrate, and methyl valerate;

ether compounds such as diethylether, di-n-propyl ether, diisopropyl ether, di-n-butyl ether, diisobutyl ether, methylpropyl ether, ethylpropyl ether, methybutyl ether, methylpentyl ether, ethylbutyl ether, propylbutyl ether, methylcyclopentyl ether, methylcyclohexyl ether, ethylcyclopentyl ether, ethylcyclohexyl ether, propylcyclopentyl ether, propylcyclohexyl ether, butylcyclopentyl ether, butylcyclohexyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, triethylene glycol dimethyl ether, triethylene glycol diethyl ether, tetrahydrofuran, methyltetrahydrofuran, tetrahydropyran, methyltetrahydropyran, 1,4-dioxane, and dimethyl-1,4-dioxane; and amide compounds such as dimethylformamide, dimethylacetamide, N-methylpyrrolidone, and 1,3-dimethyl-2-imidazolidinone.

Conversely, use of an aromatic hydrocarbon or an alcohol compound in the reaction solvent is not preferable because of their acylation by the action of the catalyst.

In an embodiment of the present invention, one selected from the foregoing or a mixture of two or more of there at an arbitrary ratio can be used as the reaction solvent.

Alternatively, the reaction may be performed only with the α-hydroxycarboxylic acid ester, the acylating agent, and the catalyst, without use of a reaction solvent, in the absence of a solvent. In consideration of the time and effort of recovery, purification, reuse, and the like of the reaction solvent, the reaction is preferably performed in the absence of a solvent.

A range of the reaction temperature of the present production method is preferably from −50 to 300° C., more preferably from −30 to 200° C., further preferably from 0 to 100° C., further more preferably from 20 to 90° C.

The reaction mode used in the present production method is not particularly limited, and a known reaction mode can be used. The reaction mode may be either of a flow reaction mode or a batch reaction mode. With appropriate combination of the type and amount of the α-hydroxycarboxylic acid ester, the acylating agent, the catalyst, and optionally, a reaction solvent, the reaction can be performed while the components are allowed to be continuously flow through or charged into the reactor.

More specific examples of the reaction method include:
(i) a method in which an α-hydroxycarboxylic acid ester, an acylating agent, and a catalyst are charged into a reactor in a batch manner to perform the reaction, (ii) a method in which an α-hydroxycarboxylic acid ester and a catalyst are charged first to a reactor, and then an acylating agent is supplied continuously or in portions to the reactor to perform the reaction, (iii) a method in which an acylating agent and a catalyst are charged first to a reactor, and then an α-hydroxycarboxylic acid ester is supplied continuously or in portions to the reactor to perform the reaction; and (iv) a method in which an α-hydroxycarboxylic acid ester and an acylating agent are charged first to a reactor, and then a catalyst alone or a solution including a catalyst dissolved in a reaction solvent is supplied continuously or in portions to the reactor to perform the reaction.

The reaction of the present production method is an exothermic reaction. Performing this reaction industrially requires heat removal, and thus, a known heat removal method can be used as appropriate in combination with the reaction mode.

The method for purifying the α-hydroxycarboxylic acid ester formed by the production method is also not particularly limited, and a known purification method such as extraction or distillation can be used without restriction.

The present inventor has attempted an acetylation (acylation) reaction of a compound having a tert-hydroxyl group (the carbon at the α-position of the hydroxyl group is not bonded to hydrogen), that is, 2-methyl-1phenyl-2 propanol (dimethylbenzylcarbinol), 2,6-dimethyl-2-heptanol, and 2-methyl-2-butanol (tert-amyl alcohol), using anhydrous iron (III) chloride catalyst and acetic anhydride.

In the present production method, when these alcohols are employed under a reaction condition under which the α-acyloxycarboxylic acid ester can be formed in an particularly high reaction yield, the yield of the acetylated product remains at 70 to 80%, and other various by-products are formed as a result, such as olefin compounds containing a plurality of isomers formed by the dehydration reaction of the alcohol and halides in which the hydroxyl group is substituted with the halogen element in the catalyst. The present inventor has confirmed that the acylation reaction of the tertiary alcohol compound is not necessarily easy and an intended compound is not selectively provided.

In an embodiment of the present invention, it is discovered that esterification of an α-hydroxycarboxylic acid ester with a particular acylating agent in the presence of a specific catalyst yields an acylated product in an extremely high yield.

EXAMPLES

Hereinafter, the present invention will be described in further detail with reference to examples, but the present invention is not limited to these examples.

The reaction performance was evaluated according to the following equations.

Raw material conversion (%)=[1−(number of moles of raw material in reaction solution)/(number of moles of raw material in raw material solution charged)]×100%

Reaction yield (%)=[(number of moles of product material in reaction solution)/(number of moles of raw material in raw material solution charged)]×100%

<Gas Chromatography (GC) Analysis>
Apparatus: GC-2010 (available from Shimadzu Corporation, trade name)
Detector: FID
Column: DB-1 (capillary column available from J&W Scientific, Inc., trade name)(0.25 mmφ×60 m×0.25 μm)
The peaks were identified using the standards.

Reference Example 1: Synthesis of Isopropyl α-hydroxyisobutyrate 118.0 g of methyl α-hydroxyisobutyrate (available from Mitsubishi Gas Chemical Company, Inc., hereinafter also referred to as "MHIB"), 141.0 g of isopropanol (available from FUJIFILM Wako Pure Chemical Corporation), and 1.29 g of titanium tetraisopropoxide (available from FUJIFILM Wako Pure Chemical Corporation) were charged in 500 ml glass flask equipped with a distillation tube and a stirrer. A transesterification reaction was performed under normal pressure with heating and refluxing. The reaction was performed for 50 hours while methanol produced was extracted out of the system. As a result, isopropyl α-hydroxyisobutyrate (hereinafter, iPHIB) was obtained at a reaction yield of 97.4% by the reaction of Formula (9) below. After water was added to the reaction system to deactivate the catalyst, distillation was performed under reduced pressure to obtain 101.0 g of isopropyl α-hydroxyisobutyrate (purity by GC analysis (hereinafter, also referred to as GC purity): 99.6%) as the fraction at 40 mmHg (53.3 hPa) and 65° C.

[Chem. 13]

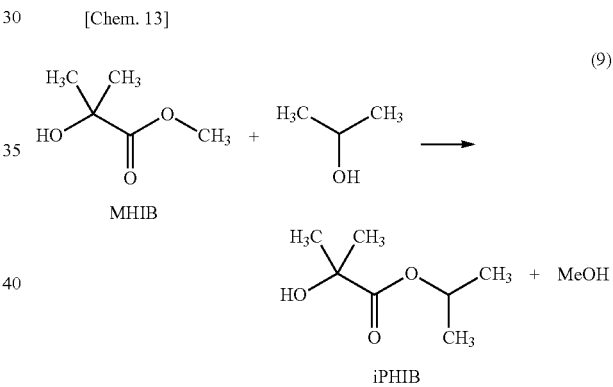

(9)

Example 1: Synthesis of Isopropyl α-Acetoxyisobutyrate 15.2 g of isopropyl α-hydroxyisobutyrate (hereinafter, also referred to as "iPHIB") prepared in Reference Example 1, 11.7 g of acetic anhydride (available from FUJIFILM Wako Pure Chemical Corporation), and 0.055 g of anhydrous iron (III) chloride (ferric chloride, available from FUJIFILM Wako Pure Chemical Corporation) were charged in a 100 ml glass flask equipped with a condenser and a stirrer. The reaction was performed for 4 hours under stirring while the temperature of the flask was maintained at 15° C. under normal pressure. As a result, isopropyl α-acetoxyisobutyrate (hereinafter, also referred to as iPAIB) was obtained at a conversion of the raw material iPHIB of 100% and a reaction yield of 99.1% by the reaction of Formula (10). Then, a washing operation was performed three times with a 10% aqueous solution of sodium hydrogen carbonate and twice with a saturated aqueous solution of sodium chloride. The washed product was dried over magnesium sulfate and then concentrated. Subsequently, distillation was performed under reduced pressure to obtain 16.8 g of iPAIB (GC purity: 99.9%) as the fraction at 47 hPa and 95° C.

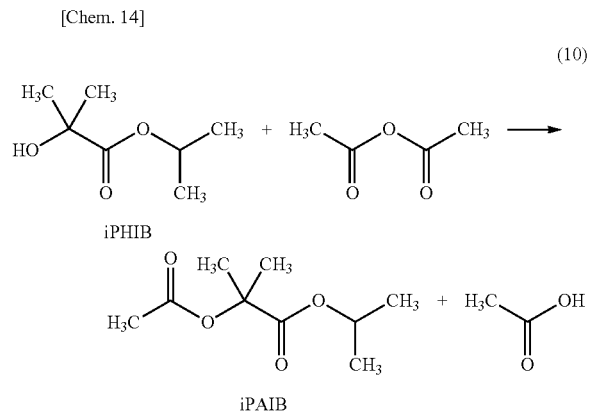

<Examples 2 to 3 and Comparative Examples 1 to 8: Synthesis of Isopropyl α-Acetoxyisobutyrate> iPAIB was synthesized, using the same reaction apparatus as in Example 1, in the same manner as in Example 1, except that iPHIB prepared in Reference Example 1, acetic anhydride (available from FUJIFILM Wako Pure Chemical Corporation) and various catalysts (all available from FUJIFILM Wako Pure Chemical Corporation) and reaction conditions were changed as shown in Table 1. The reaction conditions at that time, the conversion of raw material iPHIB, and the yield of iPAIB produced were summarized in Table 1.

0.069 g of anhydrous iron (III) chloride (ferric chloride, available from FUJIFILM Wako Pure Chemical Corporation) were charged in a 100 ml glass flask equipped with a condenser and a stirrer. The reaction was performed for 22.7 hours under stirring while the temperature of the flask was maintained at 15° C. under normal pressure. As a result, methyl ca-isobutyryloxyisobutyrate (hereinafter, also referred to as "MiBIB") was obtained at a conversion of the raw material of 100% and a reaction yield of 99.6% by the reaction of Formula (11) below.

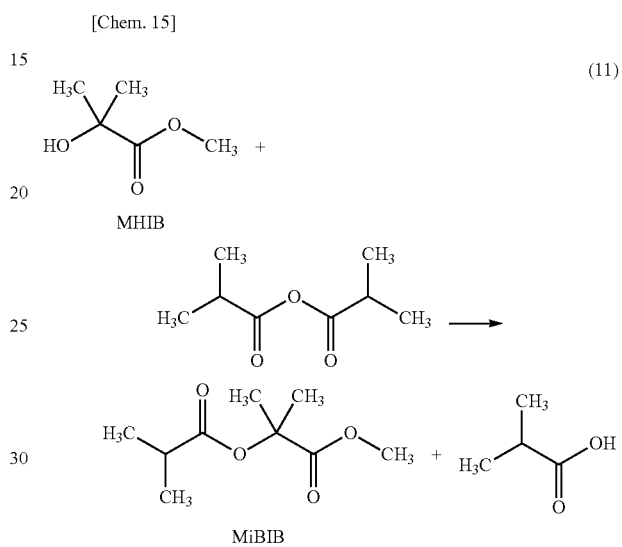

TABLE 1

| | Raw material charged | | | Catalyst | Reaction conditions | | Conversion of | Yield of |
|---|---|---|---|---|---|---|---|---|---|
| | iPHIB (g) | Acetic anhydride (g) | Catalyst species | amount (g) | Catalyst/iPHIB (Molar ratio) | Temperature (° C.) | Time (hr) | raw material iPHIB | produced iPAIB |
| Example 1 | 15.2 | 11.7 | Iron (III) chloride (FeCl$_3$) | 0.055 | $0.33 \times 10^{-2}$ | 15 | 4.0 | 100% | 99.1% |
| Example 2 | 15.7 | 12.0 | Iron (III) chloride (FeCl$_3$) | 0.004 | $0.02 \times 10^{-2}$ | 60 | 2.0 | 100% | 99.5% |
| Example 3 | 15.1 | 11.6 | Iron (III) chloride (FeCl$_3$) | 0.022 | $0.13 \times 10^{-2}$ | 60 | 0.42 | 100% | 99.6% |
| Comparative Example 1 | 15.3 | 11.8 | Zinc chloride (ZnCl$_2$) | 0.062 | $0.44 \times 10^{-2}$ | 60 | 3.0 | 62.6% | 60.4% |
| Comparative Example 2 | 15.7 | 12.1 | Zinc chloride (ZnCl$_2$) | 0.10 | $0.68 \times 10^{-2}$ | 60 | 1.5 | 99.3% | 98.5% |
| Comparative Example 3 | 15.3 | 11.7 | 85% Phosphoric acid | 0.029 | $0.24 \times 10^{-2}$ | 60 | 5.0 | 95.9% | 94.4% |
| Comparative Example 4 | 15.3 | 11.7 | 85% Phosphoric acid | 0.050 | $0.41 \times 10^{-2}$ | 60 | 4.5 | 98.8% | 97.0% |
| Comparative Example 5 | 15.1 | 11.6 | Copper(II) chloride (CuCl$_2$) | 0.55 | $4.0 \times 10^{-2}$ | 60 | 17.9 | 91.2% | 90.5% |
| Comparative Example 6 | 15.3 | 11.7 | Cerium chloride heptahydrate (CeCl$_3$·7H$_2$O) | 0.53 | $1.4 \times 10^{-2}$ | 60 | 19.6 | 95.9% | 92.3% |
| Comparative Example 7 | 15.2 | 11.6 | Neodymium chloride hexahydrate (NdCl$_3$·6H$_2$O) | 0.66 | $1.8 \times 10^{-2}$ | 60 | 19.6 | 98.5% | 96.0% |
| Comparative Example 8 | 15.2 | 11.7 | N,N-dimethyl-4-aminopyridine | 0.65 | $5.1 \times 10^{-2}$ | 60 | 20.4 | 94.4% | 90.7% |

Example 4: Synthesis of Methyl α-Isobutyryloxyisobutyrate 12.6 g of MHIB (available from Mitsubishi Gas Chemical Company, Inc.), 18.5 g of isobutyric anhydride (available from FUJIFILM Wako Pure Chemical Corporation), and Example 5 and Comparative Examples 9 to 14: Synthesis of Methyl α-Isobutyryloxyisobutyrate MiBIB was synthesized, using the same reaction apparatus as in Example 4, in the same manner as in Example 4, except that MHIB (available from Mitsubishi Gas Chemical Company, Inc.), isobutyric anhydride (available from FUJI-FILM Wako Pure Chemical Corporation), and various catalysts (all available from FUJIFILM Wako Pure Chemical Corporation) and reaction conditions were changed as shown in Table 2. The reaction conditions at that time, the conversion of the raw material MHIB, and the yield of MiBIB produced were summarized in Table 2.

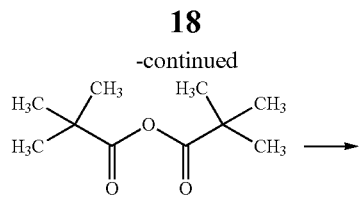

TABLE 2

| | Raw material charged | | Catalyst | | Reaction conditions | | Conversion of | Yield of |
| | Isobutyric | | | amount | Catalyst/MHIB | Temperature | Time | raw material | MiBIB |
| | MHIB (g) | anhydride (g) | Catalyst species | (g) | (Molar ratio) | (° C.) | (hr) | MHIB | produced |
|---|---|---|---|---|---|---|---|---|---|
| Example 4 | 12.6 | 18.5 | Iron (III) chloride (FeCl$_3$) | 0.069 | $0.40 \times 10^{-2}$ | 15 | 22.7 | 100% | 99.6% |
| Example 5 | 12.7 | 18.6 | Iron (III) chloride (FeCl$_3$) | 0.028 | $0.16 \times 10^{-2}$ | 60 | 0.43 | 100% | 99.2% |
| Comparative Example 9 | 12.9 | 19.0 | Zinc chloride (ZnCl$_2$) | 0.17 | $1.11 \times 10^{-2}$ | 60 | 6.3 | 95.6% | 93.2% |
| Comparative Example 10 | 12.9 | 19.0 | Zinc chloride (ZnCl$_2$) | 0.17 | $1.11 \times 10^{-2}$ | 60 | 20.0 | 100% | 98.2% |
| Comparative Example 11 | 13.05 | 19.2 | N,N-dimethyl-4-aminopyridine | 0.67 | $5.0 \times 10^{-2}$ | 60 | 6.3 | 93.8% | 90.2% |
| Comparative Example 12 | 13.05 | 19.2 | N,N-dimethyl-4-aminopyridine | 0.67 | $5.0 \times 10^{-2}$ | 60 | 20.0 | 99.3% | 96.0% |
| Comparative Example 13 | 12.8 | 18.9 | Cerium chloride heptahydrate (CeCl$_3$•7H$_2$O) | 0.43 | $1.1 \times 10^{-2}$ | 60 | 19.7 | 73.6% | 69.9% |
| Comparative Example 14 | 13.6 | 20.0 | Neodymium chloride hexahydrate (NdCl$_3$•6H$_2$O) | 0.43 | $1.3 \times 10^{-2}$ | 60 | 19.7 | 73.9% | 71.0% |

Example 6: Synthesis of Methyl α-Pivaloyloxyisobutyrate 10.3 g of MHIB (available from Mitsubishi Gas Chemical Company, Inc.), 17.9 g of pivalic anhydride (available from FUJIFILM Wako Pure Chemical Corporation), and 0.037 g of anhydrous iron (III) chloride (ferric chloride, available from FUJIFILM Wako Pure Chemical Corporation) were charged in a 100 ml glass flask equipped with a condenser and a stirrer. The reaction was performed for 4.8 hours under stirring while the temperature of the flask was maintained at 60° C. under normal pressure. As a result, methyl α-pivaloyloxyisobutyrate (hereinafter, also referred to as "MPIB") was obtained at a conversion of the raw material of 100% and a reaction yield of 99.2% by the reaction of Formula (12) below.

[Chem. 16]

(12)

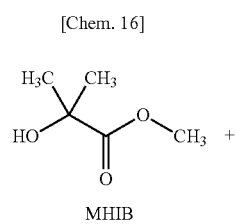

MHIB

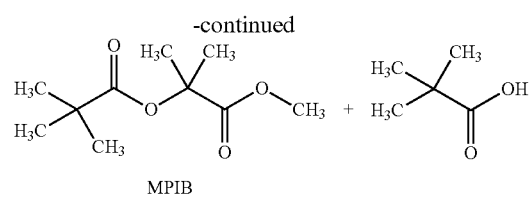

MPIB

Examples 7 to 12 and Comparative Examples 15 to 18: Synthesis of Methyl α-Pivaloyloxyisobutyrate MPIB was synthesized, using the same reaction apparatus as in Example 6, in the same manner as in Example 6, except that MHIB (available from Mitsubishi Gas Chemical Company, Inc.), pivalic anhydride (available from FUJIFILM Wako Pure Chemical Corporation), and various catalysts (all available from FUJIFILM Wako Pure Chemical Corporation) and reaction conditions were changed as shown in Table 3. The reaction conditions at that time, the conversion of the raw material MHIB, and the yield of MPIB produced were summarized in Table 3.

TABLE 3

| | Raw material charged | | Catalyst | | Reaction conditions | | Conversion of | Yield of |
| | Pivalic | | | amount | Catalyst/MHIB | Temperature | Time | raw material | MPIB |
| | MHIB (g) | anhydride (g) | Catalyst species | (g) | (Molar ratio) | (° C.) | (hr) | MHIB | produced |
|---|---|---|---|---|---|---|---|---|---|
| Example 6 | 10.3 | 17.9 | Iron (III) chloride (FeCl$_3$) | 0.037 | $0.26 \times 10^{-2}$ | 60 | 4.8 | 100% | 99.2% |
| Example 7 | 10.2 | 17.7 | Iron (III) chloride (FeCl$_3$) | 0.057 | $0.41 \times 10^{-2}$ | 60 | 2.5 | 100% | 98.6% |

TABLE 3-continued

| | Raw material charged | | | Catalyst | Reaction conditions | | | Conversion of | Yield of |
|---|---|---|---|---|---|---|---|---|---|
| | MHIB (g) | Pivalic anhydride (g) | Catalyst species | amount (g) | Catalyst/MHIB (Molar ratio) | Temperature (°C.) | Time (hr) | raw material MHIB | MPIB produced |
| Example 8 | 10.2 | 17.7 | Iron (III) chloride (FeCl$_3$) | 0.084 | $0.60 \times 10^{-2}$ | 60 | 3.0 | 100% | 99.4% |
| Example 9 | 10.3 | 17.8 | Iron (III) chloride hexahydrate (FeCl$_3$·6H$_2$O) | 0.086 | $0.37 \times 10^{-2}$ | 60 | 1.3 | 100% | 98.6% |
| Example 10 | 10.4 | 18.0 | Iron (III) chloride hexahydrate (FeCl$_3$·6H$_2$O) | 0.16 | $0.66 \times 10^{-2}$ | 60 | 0.8 | 100% | 99.6% |
| Example 11 | 10.2 | 17.6 | Iron (III) bromide (FeBr$_3$) | 0.066 | $0.26 \times 10^{-2}$ | 60 | 1.2 | 100% | 98.8% |
| Example 12 | 10.2 | 17.6 | Iron (III) bromide (FeBr$_3$) | 0.13 | $0.70 \times 10^{-2}$ | 60 | 0.9 | 100% | 99.2% |
| Comparative Example 15 | 10.1 | 17.4 | Zinc chloride (ZnCl$_2$) | 0.54 | $4.7 \times 10^{-2}$ | 60 | 19 | 100% | 98.2% |
| Comparative Example 16 | 10.3 | 17.9 | Zinc chloride (ZnCl$_2$) | 0.10 | $0.84 \times 10^{-2}$ | 60 | 86 | 89.3% | 88.5% |
| Comparative Example 17 | 10.5 | 18.2 | N,N-dimethyl-4-aminopyridine | 0.57 | $5.25 \times 10^{-2}$ | 60 | 86 | 35.2% | 31.2% |
| Comparative Example 18 | 10.0 | 17.3 | Neodymium chloride hexahydrate (NdCl$_3$·6H$_2$O) | 0.56 | $1.85 \times 10^{-2}$ | 60 | 40 | 15.9% | 11.5% |

Example 13: Synthesis of Isopropyl α-Acetoxyisobutyrate 250 g of iPHIB prepared in the same manner as in Reference Example 1 and 0.0277 g of anhydrous iron (III) chloride (ferric chloride, available from FUJIFILM Wako Pure Chemical Corporation) (molar concentration with respect to iPHIB: 0.010%) were placed in a 3-neck flask having an internal volume of 1 liter equipped with a condenser and a stirrer, and then the temperature was raised to 55° C. 192 g of acetic anhydride (available from FUJIFILM Wako Pure Chemical Corporation) was added dropwise with a liquid feeding pump at a rate of 64 g per hour over 3 hours, and the reaction was performed at a liquid temperature of 60° C. The composition of the reaction liquid was confirmed by GC analysis over time. After 5 hours from the start of the dropwise addition, formation of iPAIB was confirmed with disappearance of the raw material iPHIB (conversion of iPHIB: 100%) and a reaction yield of 99.6%.

After cooling, the reaction liquid was poured into an aqueous solution of sodium carbonate, and the mixture was subjected to a washing operation with water by liquid separation 4 times. Thereafter, a washing operation with ion exchanged water was performed once. The crude product after the liquid separation was transferred to a three-neck flask having an inner volume of 1 liter equipped with the distillation tower of 25 mm in diameter and 300 mm in length packed with McMahon packing, and subjected to vacuum distillation to give 276.7 g of iPAIB (GC purity: 99.9%) as a fraction at 55 hPa and 97° C.

INDUSTRIAL APPLICABILITY

The method of the present invention can provide a method for producing an α-acyloxycarboxylic acid ester, the method being efficient and excellent in economic efficiency.

The invention claimed is:

1. A method for producing an α-acyloxycarboxylic acid ester compound of Formula (1), the method comprising:
    reacting an α-hydroxycarboxylic acid ester compound of Formula (2) with an acylating agent of Formula (3) in the presence of a catalyst comprising an iron halide compound,

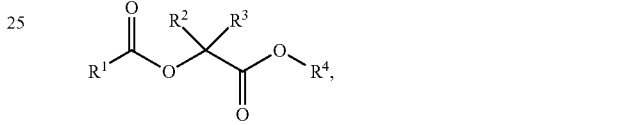

where $R^1$ is a hydrogen atom, a methyl group, an ethyl group, a n-propyl group, an isopropyl group, or a tert-butyl group,
$R^2$ and $R^3$ are each independently a methyl group or an ethyl group,
$R^4$ is a linear, branched, or cyclic alkyl group having from 1 to 6 carbon atoms,

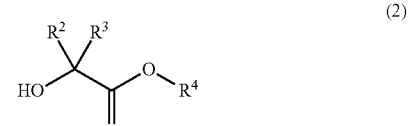

Z is chlorine, bromine, or an acyloxy group represented by $R^1C(=O)O-$,
wherein a molar ratio of iron atoms in the iron halide compound to the α-hydroxycarboxylic acid ester compound is from $50 \times 10^{-6}$ to $0.7 \times 10^{-2}$.

2. The method according to claim 1, wherein the catalyst comprises at least one selected from the group consisting of
    (i) an iron halide compound is at least one selected from the group consisting of FeCl$_3$, FeBr$_3$, FeCl$_2$, and FeBr$_2$,
    (ii) a hydrate of the iron halide compound,
    (iii) a complex of the iron halide compound with a ligand coordinated thereto, and
    (iv) a mixture of any one of (i)-(iii).

3. The method according to claim 1, wherein the catalyst comprises at least one selected from the group consisting of FeCl$_3$, a hydrate thereof, a complex with a ligand coordinated thereto, and a mixture thereof.

4. The method according to claim 1, wherein the acylating agent is a carboxylic anhydride of Formula (7):

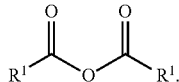

(7)

5. The method according to claim 1, wherein, in the ester compound of Formula (1), $R^4$ is a methyl group, an ethyl group, a n-propyl group, an isopropyl group, a n-butyl group, an isobutyl group, a sec-butyl group, a tert-butyl group, a 2-methylbutyl group, a 3-methylbutyl group, a 2,2-dimethylpropyl group, a n-hexyl group, a 2-methylpentyl group, a 4-methylpentan-2-yl group, a cyclopentyl group, or a cyclohexyl group.

6. The method according to claim 1, wherein $R^2$ and $R^3$ are both methyl groups in the ester compound of Formula (1).

7. The method according to claim 1, wherein the reacting is performed in absence of a solvent.

8. The method according to claim 2, wherein the acylating agent is a carboxylic anhydride of Formula (7):

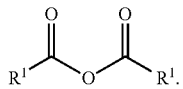

(7)

9. The method according to claim 3, wherein the acylating agent is a carboxylic anhydride of Formula (7):

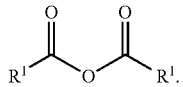

(7)

10. The method according to claim 2, wherein, in the ester compound of Formula (1), $R^4$ is a methyl group, an ethyl group, a n-propyl group, an isopropyl group, a n-butyl group, an isobutyl group, a sec-butyl group, a tert-butyl group, a 2-methylbutyl group, a 3-methylbutyl group, a 2,2-dimethylpropyl group, a n-hexyl group, a 2-methylpentyl group, a 4-methylpentan-2-yl group, a cyclopentyl group, or a cyclohexyl group.

11. The method according to claim 3, wherein, in the ester compound of Formula (1), $R^4$ is a methyl group, an ethyl group, a n-propyl group, an isopropyl group, a n-butyl group, an isobutyl group, a sec-butyl group, a tert-butyl group, a 2-methylbutyl group, a 3-methylbutyl group, a 2,2-dimethylpropyl group, a n-hexyl group, a 2-methylpentyl group, a 4-methylpentan-2-yl group, a cyclopentyl group, or a cyclohexyl group.

12. The method according to claim 4, wherein, in the ester compound of Formula (1), $R^4$ is a methyl group, an ethyl group, a n-propyl group, an isopropyl group, a n-butyl group, an isobutyl group, a sec-butyl group, a tert-butyl group, a 2-methylbutyl group, a 3-methylbutyl group, a 2,2-dimethylpropyl group, a n-hexyl group, a 2-methylpentyl group, a 4-methylpentan-2-yl group, a cyclopentyl group, or a cyclohexyl group.

13. The method according to claim 2, wherein $R^2$ and $R^3$ are both methyl groups in the ester compound of Formula (1).

14. The method according to claim 3, wherein $R^2$ and $R^3$ are both methyl groups in the ester compound of Formula (1).

15. The method according to claim 4, wherein $R^2$ and $R^3$ are both methyl groups in the ester compound of Formula (1).

16. The method according to claim 5, wherein $R^2$ and $R^3$ are both methyl groups in the ester compound of Formula (1).

17. The method according to claim 2, wherein the reacting is performed in absence of a solvent.

18. The method according to claim 3, wherein the reacting is performed in absence of a solvent.

19. The method according to claim 4, wherein the reacting is performed in absence of a solvent.

20. The method according to claim 5, wherein the reacting is performed in absence of a solvent.

* * * * *